United States Patent [19]
Salce et al.

[11] Patent Number: 5,088,114
[45] Date of Patent: Feb. 18, 1992

[54] DISPOSABLE FACESHIELD AND METHOD OF MANUFACTURE THEREOF

[75] Inventors: Arthur J. Salce; Richard T. Metcalfe, both of Southbridge, Mass.

[73] Assignee: Cabot Safety Corporation, Southbridge, Mass.

[21] Appl. No.: 464,965

[22] Filed: Jan. 16, 1990

Related U.S. Application Data

[60] Division of Ser. No. 206,597, Jun. 14, 1988, which is a continuation-in-part of Ser. No. 152,624, Feb. 5, 1988.

[51] Int. Cl.⁵ .......................... A61F 9/00; A61F 9/04; A61F 9/06
[52] U.S. Cl. .............................. 2/9; 2/426; 2/427; 2/429; 2/430; 2/447
[58] Field of Search .................. 2/9, 10, 12, 171, 173, 2/185 R, 199, 206, 424, 426, 427, 428, 429, 430, 447

[56] References Cited

U.S. PATENT DOCUMENTS

| | | | |
|---|---|---|---|
| D. 228,700 | 10/1973 | Gager | 2/10 X |
| 583,590 | 6/1897 | Bennett | 2/447 |
| 2,296,634 | 9/1942 | Fink | 2/447 |
| 2,390,599 | 12/1945 | Lewis | 2/447 X |
| 2,598,265 | 5/1952 | Jones | 2/427 |
| 2,617,100 | 11/1952 | Moeller | 2/447 |
| 2,680,882 | 6/1954 | Hirschmann et al. | 2/447 X |
| 3,015,105 | 1/1962 | Rogowski | 2/9 |
| 3,103,667 | 9/1963 | Rogowski | 2/9 |
| 3,152,588 | 10/1964 | Rogowski | 2/9 X |
| 3,274,614 | 9/1966 | Boyer | 2/427 |
| 3,526,449 | 9/1970 | Bollé et al. | 2/447 X |
| 3,705,760 | 12/1972 | Langendorfer et al. | 2/447 X |
| 3,774,239 | 11/1973 | Kotzar | 2/10 |
| 4,097,930 | 7/1978 | Bay | 2/10 |
| 4,630,317 | 12/1986 | Brown et al. | 2/171 X |
| 4,701,965 | 10/1987 | Landis | 2/9 |
| 4,852,186 | 8/1989 | Landis | 2/9 |

FOREIGN PATENT DOCUMENTS

| | | | |
|---|---|---|---|
| 867431 | 1/1953 | Fed. Rep. of Germany | 2/447 |
| 2142221 | 1/1973 | France | 2/10 |

Primary Examiner—Werner H. Schroeder
Assistant Examiner—Jeanette E. Chapman
Attorney, Agent, or Firm—Fishman, Dionne & Cantor

[57] ABSTRACT

A one-piece, lightweight (optionally disposable) protective faceshield is disclosed for use by the medical profession to protect against contamination from splattered body fluids. A method of making such a faceshield by vacuum-forming over a mandrel is also disclosed whereby preservation of maximum optical clarity in the viewing zone is preserved. Also disclosed are reusable and disposable headbands which attach to the one-piece protective faceshields.

36 Claims, 8 Drawing Sheets

DISPOSABLE FACESHIELD AND METHOD OF MANUFACTURE THEREOF

CROSS-REFERENCE TO RELATED APPLICATION

This is a divisional of U.S. application Ser. No. 206,597 filed June 14, 1988 which is a continuation-in-part of U.S. application Ser. No. 152,624 filed Feb. 5, 1988.

BACKGROUND OF THE INVENTION

This invention relates to a one-piece, lightweight protective faceshield, particularly one having a viewing zone of maximum optical clarity, and a method of making such a faceshield.

Various types of faceshields are known in the art, many of which are designed to protect the wearer against flying projectiles. Such faceshields are generally comprised of multi-components, such as a clear viewing/shield portion affixed to a helmet or visor unit and are generally fabricated of relatively thick, impact-resistant plastic. There are generally known two preferred methods for fabricating a faceshield with acceptable optical clarity.

In one method, the faceshield may be injection molded in a mold that has a highly polished surface. Such processes generally require that the molded part have a thickness in excess of 0.040 inch (1.02 mm) to achieve reasonable polymer flow into the mold. Other than the thickness of the part, which is acceptable for most applications, this method produces very high quality precision parts of any desired configuration.

In a second method, a blank may be taken from an optically polished flat polymer sheet (the sheet is polished usually by pressing between two platens) and formed in a curved piece (i.e. cylindrical, not spherical) by heating the blank beyond its glass transition temperature and applying force in the direction of the desired curve. This method generally retains the optics of the original polished sheet, but is only suitable for simple curved pieces and cannot be utilized where the desired piece has a complex configuration.

It is now recognized that there is a need in the medical profession (the term "medical" as used herein is intended to encompass the medical, dental and related professions) for a lightweight, preferably disposable, faceshield to protect the medical professional from splattered body fluids so as to avoid the possibility of contamination therefrom. While certainly many of the heretofore known goggles and faceshields might serve this purpose, such products tend to be bulkier and heavier than is desired by the medical professional and are far too costly to be considered disposable.

SUMMARY OF THE INVENTION

The above-discussed and other problems and deficiencies of the prior art are overcome or alleviated by the inexpensive one-piece, lightweight protective faceshield of the present invention which is particularly well suited for use in the medical profession.

The present invention comprises a one-piece, lightweight protective faceshield comprising a curved brow member adapted to substantially conform with and contact a wearer's forehead; a faceshield body extending outwardly and downwardly from said brow member and integral therewith, said faceshield body being adapted to cover at least a portion of the wearer's face without contacting any part thereof below the forehead; and means for retaining said brow member in contact with the wearer's forehead.

The present invention also comprises a one-piece, lightweight eye protective shield comprising an eye protective member adapted to shield a wearer's eyes from splattered liquid or soft foreign matter, said eye protective member being fabricated of a transparent thermoplastic film less than 0.030 inch (0.76 mm) thick and having an integral viewing portion disposed in the wearer's viewing path, wherein said viewing portion has retained the same or better optical clarity as the thermoplastic film from which said shield is fabricated.

In addition, the present invention comprises a method of making a protective shield with a viewing portion of maximum optical clarity which comprises vacuum forming a transparent thermoplastic film over a forming mandrel of the desired shape wherein said forming mandrel is designed such that said viewing portion of said protective shield does not contact any part thereof.

In a preferred embodiment, the one-piece, disposable faceshield is retained or secured onto the wearer's head by either a reusable or disposable headband. The reusable headband comprises a visor having a pair of opposed resilient arms for securing to the head. Suitable attaching means such as a series of studs or snap shaped protrusions are provided to the visor and faceshield for easily attaching and removing faceshields from the visor. The disposable headband comprises a semi circular piece terminating at a pair of opposed resilient arms. This disposable headband may be ultrasonically welded or otherwise attached to the faceshield. Alternatively, the disposable headband may be injection or otherwise molded to the previously vacuum formed one-piece faceshield.

The above discussed and other features and advantages of the present invention will be appreciated and understood by those of ordinary skill in the art from the following detailed description and drawings.

BRIEF DESCRIPTION OF THE DRAWINGS

Referring now to the drawings, wherein like elements are numbered alike in the several Figures.

DESCRIPTION OF THE PREFERRED EMBODIMENTS

Figure 1:
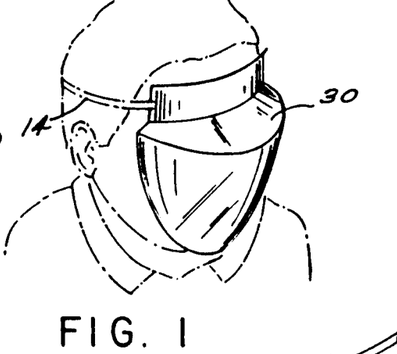
FIG. 1 illustrates a faceshield of the present invention as it would be worn by a wearer.

With reference to the drawings, the preferred faceshield of the present invention is illustrated in FIGS. 2-5. The faceshield 10 comprises a curved brow member 11 which is adapted to substantially conform with and contact a wearer's forehead, as shown in FIG. 1. The uppermost edge 12 of the curved brow member is advantageously curved away from the wearer's forehead to avoid contact of the forehead with any sharp edges which might cause discomfort. A faceshield body 13 (also referred to as eye protective shield) extends first outwardly at surface 30, then downwardly from the curved brow member and is integral therewith. The faceshield body is adapted to cover at least a portion of the wearer's face (i.e. at least the wearer's eyes) without contacting any part of the face below the forehead. When means for retaining the curved brow member against the wearer's forehead, such as elastic band 14, are affixed to the faceshield, the faceshield can be comfortably worn as shown in FIG. 1, with the curved brow member 11 providing a solid comfortable fit.

The above-described faceshield is advantageously fabricated as one-piece out of a transparent, optical grade, thermoplastic material. To keep the product lightweight and inexpensive, and optionally disposable, the faceshield should have a thickness of less than 0.030 inch (0.76 mm), preferably less than 0.020 inch (0.151 mm) and most preferably less than 0.015 inch (0.38 mm).

Looking at other features of the faceshield of the present invention, the faceshield body can be seen to comprise an upper viewing portion 15 which is disposed in the wearer's viewing path. This viewing portion is preferably bubble-shaped to preserve optical clarity as will be explained below. If the faceshield is designed to extend below the eyes, a lower portion 16 extends downwardly from the upper viewing portion. It has been found to be particularly advantageous to fabricate the lower portion 16 so that it first extends outwardly slightly from the upper viewing portion, then downwardly, as can be more clearly seen in FIG. 5, so as to create a deflecting point 17 to direct exhaled air away from the upper viewing portion.

Careful attention is required to achieve the maximum optical clarity in the viewing portion 15 since obviously any flaw or distortion in this area will detract from the usefulness and acceptance of the product. A new method of manufacturing the above-described faceshield has now been discovered which results in a viewing portion of maximum optical clarity.

As a result of this new method, it is possible to fabricate the faceshield in such a way that the viewing portion will retain the same optical clarity as the original thermoplastic film from which the faceshield is fabricated, and possibly even better optical clarity. That is, unlike other fabricating methods which can adversely affect the optics, the present method retains a good optical properties. In fact, the viewing portion of the present faceshield has a minimum resolution of 20, preferably at least 24, determined on a National Bureau of Standards Resolution Test Chart, Special Publication 374 (ANSI Z87.1-1979, Sec. 6.3.4.1.3).

This is an extremely significant discovery since, because of the thinness of the present faceshield, it cannot be fabricated using injection molding techniques in which good optics can be preserved. The only economically feasible method for fabricating a thin piece like the present faceshield is to vacuum form a thermoplastic film over a mandrel shaped to the desired configuration. This is the typical method of making items such as yogurt containers and blister packs. The problem with this method, however, is that an undesirable amount of optical degradation or distortion occurs as the film contacts the mandrel surfaces. Thus, this method would not ordinarily be suitable for fabricating pieces requiring maximum optical clarity.

The method utilized in the present invention is essentially identical to currently known vacuum forming techniques with the exception that the forming mandrel has been modified in the area corresponding to the viewing portion of the faceshield. This modification will be described later. In the typical vacuum forming process a transparent thermoplastic film is taken from a roll or sheet, heated and allowed to conform to the shape of a three-dimensional forming tool or mandrel where, after cooling, it is removed from the mandrel and die cut from the sheet.

Figure 6:
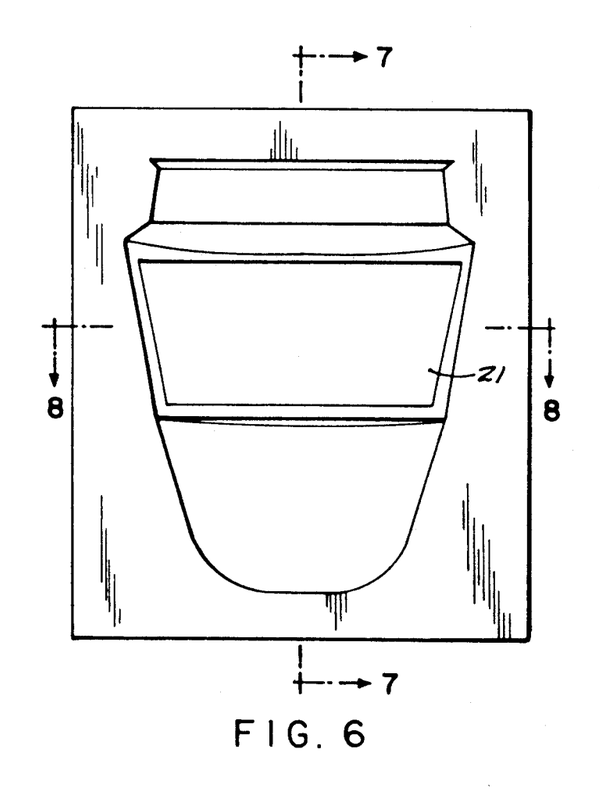
FIG. 6 is a top plan view of a forming mandrel on which the faceshield illustrated in FIG. 2 is formed.
Figure 7:
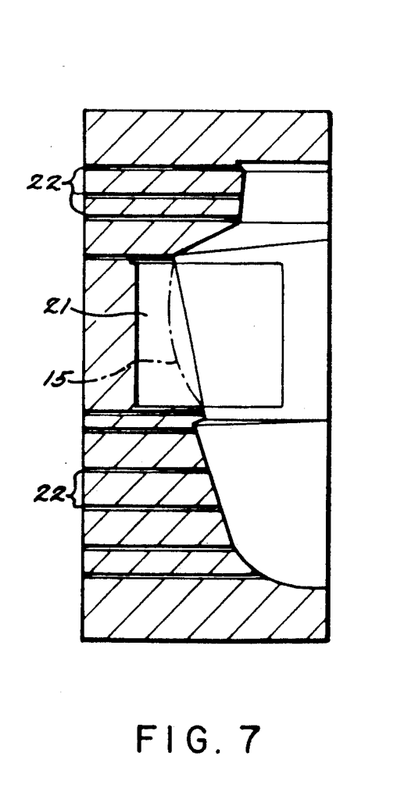
FIG. 7 is a sectional view of the forming mandrel illustrated in FIG. 6, taken along the line 7—7.
Figure 8:
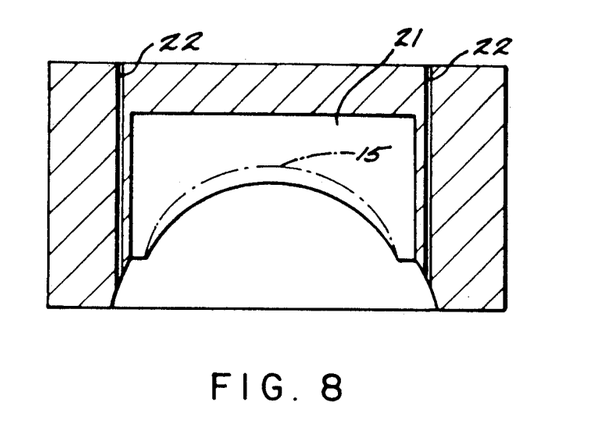
FIG. 8 is a sectional view of the forming mandrel illustrated in FIG. 6, taken along the line 8—8.
Figure 18:
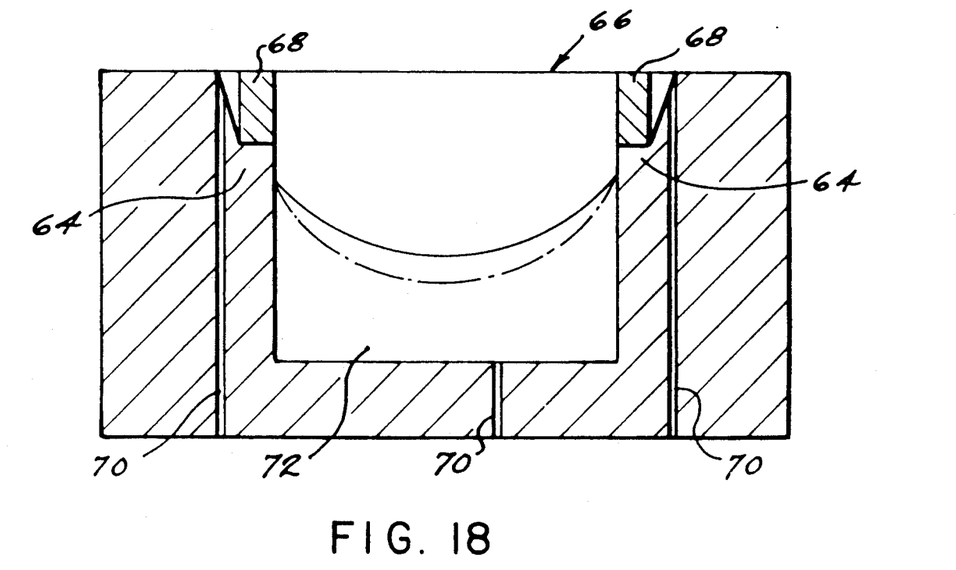
FIG. 18 is a schematic view of a mold used to form the faceshield to FIG. 10.

As shown in FIGS. 6-8, the forming mandrel 20, which is utilized to form the faceshields of the present invention, is a three-dimensional female mold made of polished cast aluminum which conforms in every respect to the desired shape of the faceshield. However, the mandrel cutaway portion (or pocket) 21, which corresponds to the viewing portion 15 of the faceshield, has been cut away so that during the forming process, the film which forms the viewing portion 15 of the faceshield, which is shown in phantom in FIGS. 7-8, sags into a bubble shape within the cutaway portion but does not contact any part of the mandrel. In this manner, the optical clarity of the original thermoplastic film is maintained, and in some cases is improved due to a stretching of the material as it sags into the cutaway portion. Vacuum holes 22 extend throughout the mandrel, except the cutaway portion, through which a vacuum can be applied to assist the conformation of the heated thermoplastic film to the mandrel surface. Optionally, a hole connecting the cutaway portion to the outside atmospheric pressure, or some other pressure source, can be employed to control the size of the bubble that forms the viewing portion as is shown in FIG. 18.

Figure 9:
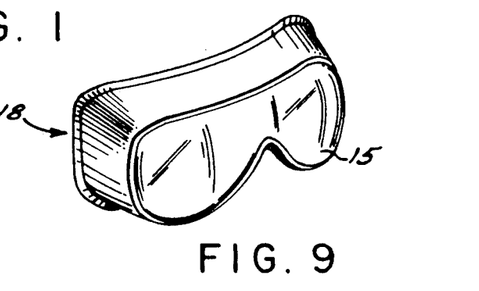
FIG. 9 is a perspective view of a goggle of the present invention having a bubble shaped viewing area.

In like manner, an eye protective shield in the form of a goggle 18, as shown in FIG. 9, can be fabricated utilizing the method of this invention. Such a goggle will have a bubble-shaped viewing portion 15 similar to the viewing portion of the faceshield described earlier.

As mentioned previously, the faceshield of the present invention may be fabricated out of any transparent, optical grade, thermoplastic film including films of polymeric resins selected from polycarbonates, polyesters, copolyesters, polyvinyl chloride, cellulose alkylates (including cellulose acetates, propionates and butyrates) polysulfones, polyether sulfones and polystyrenes. Preferred polymeric resins are polycarbonate of bisphenol-A, particularly G.E. graphic grade 8010 polycarbonate from General Electric, polyethylene terephthalate, and Kodar PETG Copolyesters 6763 from Eastman Chemical Products. Such polymeric films should have a thickness in the range of about 0.005 to 0.030, inch (0.013 to 0.76 mm), most preferably 0.005 to 0.015 inch (0.013 to 0.38 mm).

A suitable manufacturing process for the faceshield of the present invention is as follows: A transparent thermoplastic film such as Kodar P.E.T.G. Copolyester 6763, manufactured by Eastman Chemical Products, Inc., of Kingsport, Tenn. is fed from a roll form approximately 24 inches wide into a conventional vacuum forming machine. This film may be treated with a denesting agent to allow easier release from the forming tools. The film may also have a protective coating on front or back sides, or inter-leaving material to protect the film surface. These protective coatings are stripped from the film before the film is heated. The film is advanced to a heating station where it is brought beyond its glass transition temperature, which in the case of P.E.T.G. 6763 is preferably about 320° F. The heated film begins to sag at this elevated temperature and is then brought into contact with the forming tools. The forming tools can be either male or female and may be multiple in number. In this case female forming tools made of polished cast aluminum, as shown in FIGS. 6-8, are employed. These forming tools are temperature controlled at about 150° F. A vacuum of approximately 25 inches of mercury is drawn through holes 22 on the interior of the forming tools which allows outside atmospheric pressure to force the film to comply to the forming tool shape. The pocket 21 where the optical viewing portion is located has had material removed from the forming mandrel so that the film forms a natural curved shape without touching the mandrel. There are no vacuum holes entering the pocket that forms the optical viewing area. The film is withdrawn from the female forming mandrels and indexed to the next position where the parts are die cut from the film web. At the die cutting station, the preformed parts are positioned in a matched set of male and female blanking tools where they are cut from the web. It can be arranged so that the part is held slightly in the web for indexing to the final station where they are broken free. Information may be stamped on the part as desired by engraving the forming mandrel with the desired information. After the part has been die cut from the roll, a headband is attached by stapling or other means of attachment.

Figure 10:
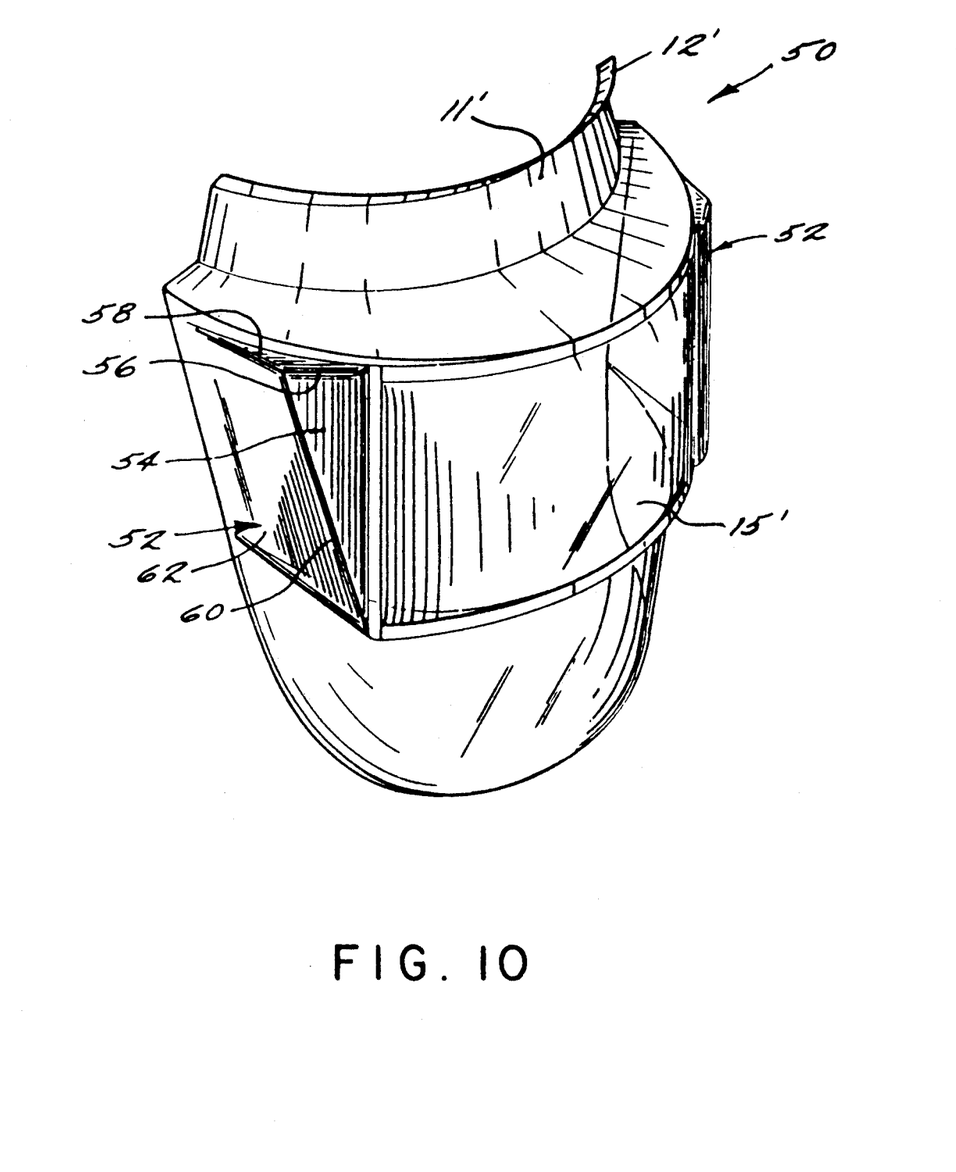
FIG. 10 is a front perspective view of another embodiment of a faceshield in accordance with the present invention.

Turning now to FIG. 10, a preferred embodiment of a disposable faceshield in accordance with the present invention is shown at 50. Faceshield 50 is similar to faceshield 10 of FIGS. 2-5 so that corresponding structural features have been identified in the same manner with the addition of a prime. An important structural distinction between faceshield 50 of FIG. 10 and faceshield 10 of FIGS. 2-5 is the presence of opposed side extensions 52 which extend outwardly from opposed side surfaces of the faceshield adjacent upper viewing portion 15'. Each side extension 52 comprises a triangularly shaped front panel 54 joined along its upper edge 56 to another triangularly shaped top panel 58; and joined along its outer side edge 60 to a substantially parallelagram shaped panel 62.

Turning to FIG. 18, side extensions 52 are formed during vacuum molding by an appropriately shaped male land 64 in the mold 66. A plug 68 applies pressure against the faceshield and land 64 to form an airtight seal so that a vacuum may be drawn through one or more channels 70 in pocket 72. As opposed to the method of molding depicted in FIGS. 6-8, it has now been found advantageous to apply a vacuum to pocket 72 which permits careful control of the optical bubble size and shape.

Figure 11:
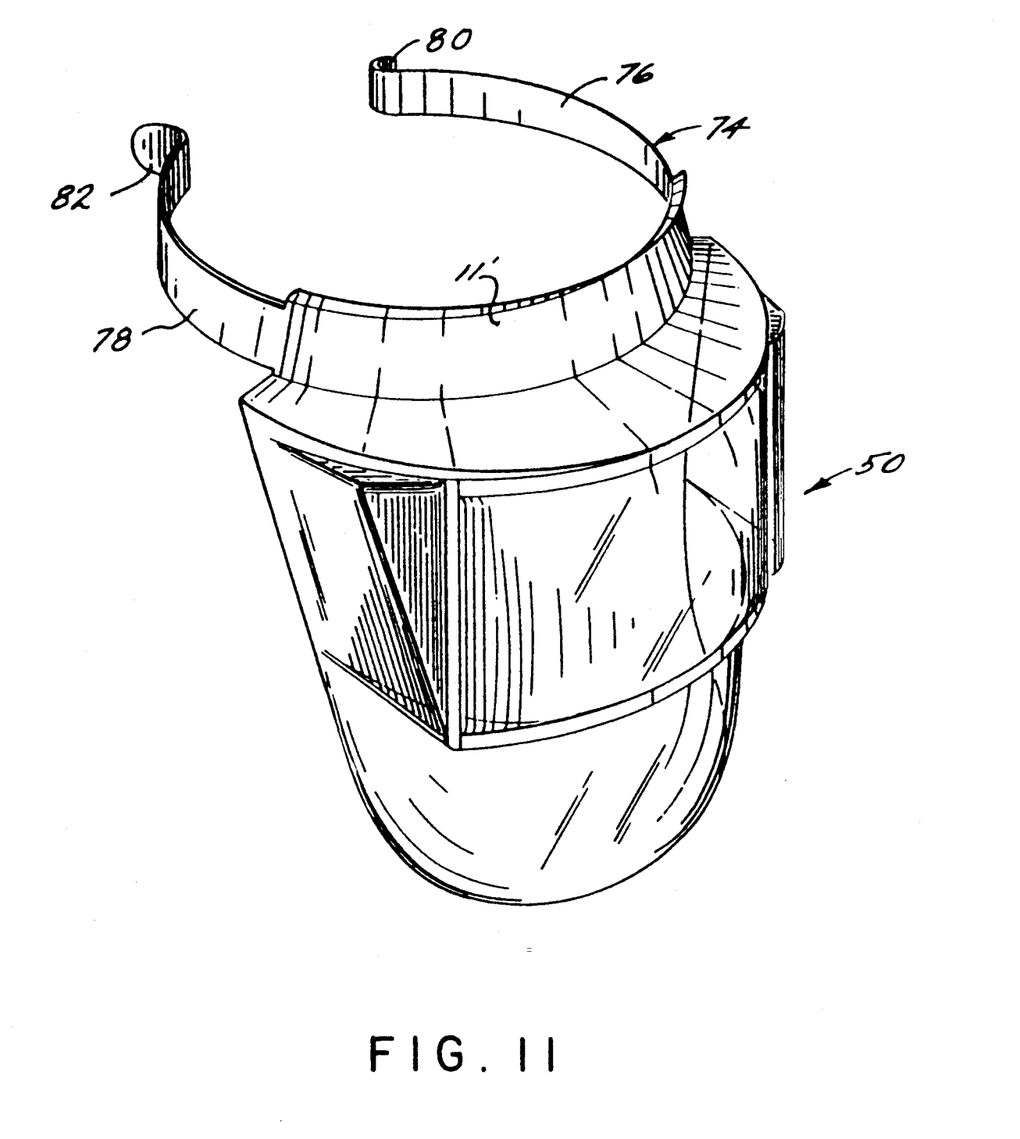
FIG. 11 is a front perspective view of a faceshield with disposable head attachment in accordance with the present invention.
Figure 12:
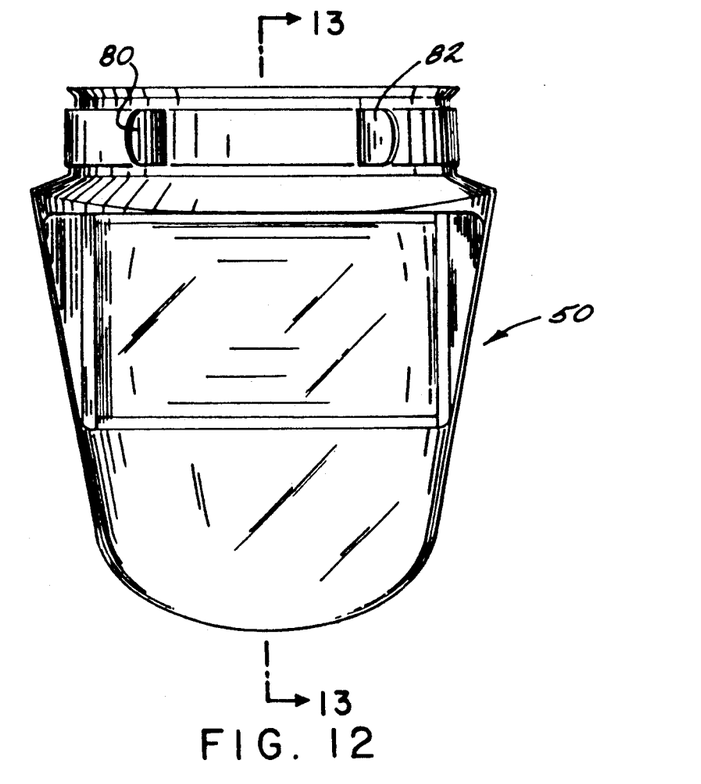
FIG. 12 is a rear elevation view of the faceshield of FIG. 11.
Figure 13:
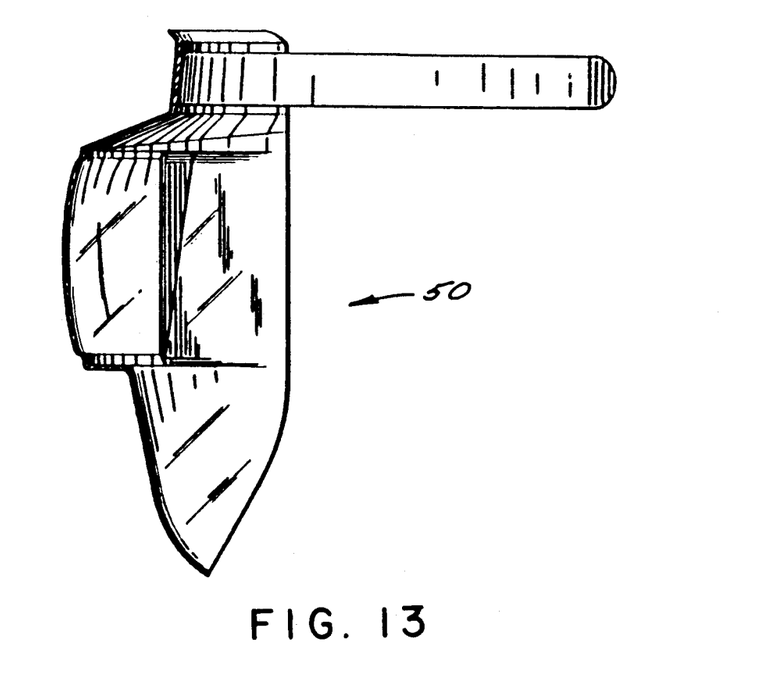
FIG. 13 is a cross sectional elevation view along the line 13—13 of FIG. 12.

Referring now to FIGS. 11-13, faceshield 50 of FIG. 10 is depicted in conjunction with a non-reusable headband 74. Headband 74 is comprised of a resilient material which is preferably plastic such as polyester, polyesterpropionate or polycarbonate. Headband 74 includes a pair of bands 76, 78 which may be part of continuous semi-circular piece or may be discrete members. In any event, headband 74 is attached to brow section 11' by any suitable method including ultrsonic bonding techniques, high frequency RF bonding techniques or by use of a suitable adhesive. Still another method of attaching headband 74 is to mold (e.g. injection mold) the headband directly to the faceshield 50. In this latter case, the previously vacuum formed faceshield would be loaded into a suitable mold; and the resilient members 76, 78 would be molded directly to the faceshield. Headband members 76 and 78 terminate at respective reverse curve sections 80 and 82 which allow easier positioning on the head.

It will be appreciated that the headband 74 of FIGS. 11-13 will allow the faceshield to be easily put on and taken off without the use of elastic bands (FIG. 1) or similar head gear thus allowing for one-handed head attachment. This is particularly advantageous when the faceshield is to be worn in conjunction with other headpieces such as nurse's caps. Thus, the resilient members 76, 78 would simply be pushed onto the wearer's head without the need to remove a previously placed headpiece (e.g. nurse's cap).

Turning now to FIGS. 14-17, still another embodiment of head attaching means for use in conjunction with the one-piece faceshield of the present invention is shown. In this embodiment, the headgear is a reusable unit 84 which is similar in appearance to a known sun visor. Headgear 84 comprises a curved circular member 86 terminating at opposed side members 89 and 90. Side members 89 and 90 terminate at opposed flared pieces 92 and 94 which are similar in appearance and function to members 80 and 82 in FIG. 11. A flanged arcuate section 96 extends outwardly of circular member 86 and has a shape corresponding to the shape of flared surface or skirt 30' of faceshield 50'.

Figure 14:
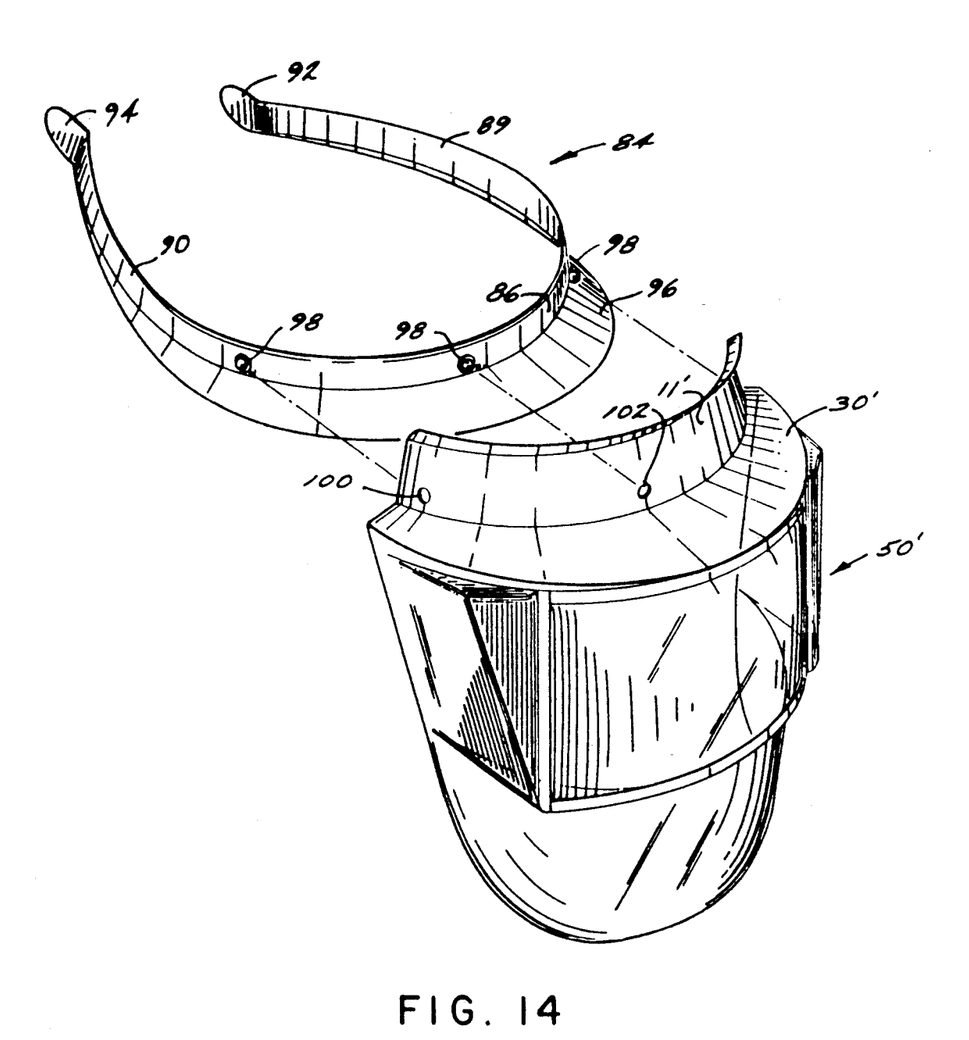
FIG. 14 is an exploded front perspective view of a faceshield with reusable head attachment in accordance with the present invention.
Figure 15:
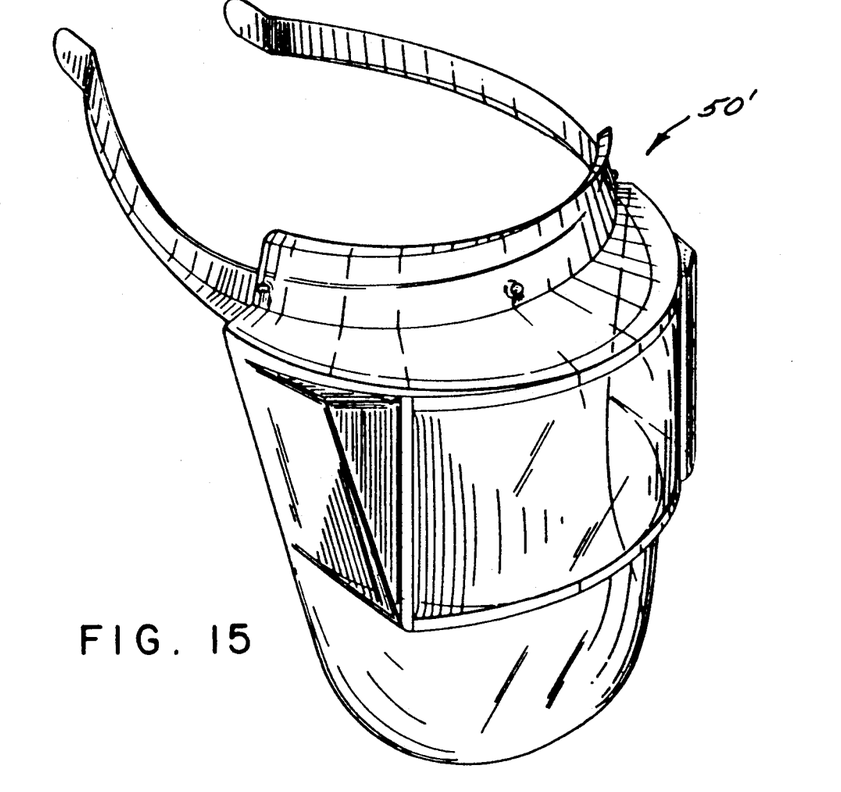
FIG. 15 is a front perspective view of the faceshield of FIG. 14.
Figure 16:
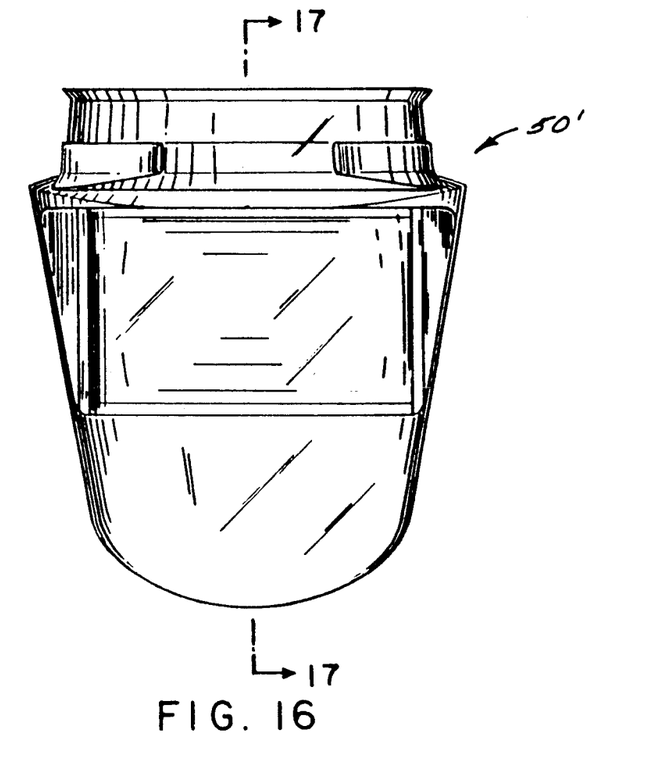
FIG. 16 is a rear elevation view of the faceshield of FIG. 14.
Figure 17:
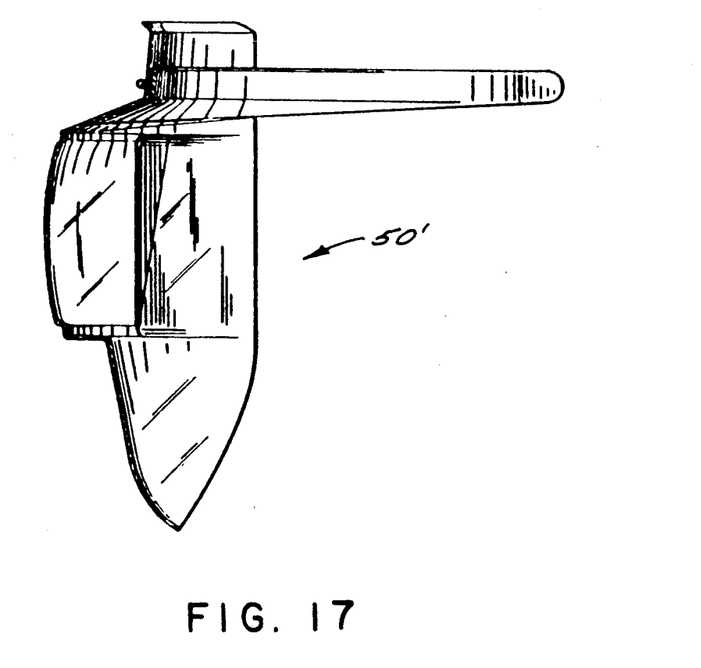
FIG. 17 is a cross sectional elevation view along the line 17-17 of FIG. 16.

Visor unit 84 includes suitable attachment means for connecting and disconnecting to disposable faceshields. Preferably, circular member 86 includes a plurality (in this case three) of studs or snap shaped protrusions 98 along the exterior thereof. Protrusions 98 could be either attached as a secondary operation or are preferably molded integrally with the visor 84. Faceshield 50' would have locating holes 100 placed along brow portion 11' which would correspond to protrusions 98; and which would be adapted to spread open, pass over studs 98 and be held firmly in place (see FIG. 15). This could be accomplished by providing four small slits 102 equally spaced about holes 100. Of course, any other suitable attachment means between visor 84 and faceshield 50 could be used. For example, the faceshield could be attached to the visor by the use of molded or discrete clips. Such clips could be attached either to the visor or the faceshield. The faceshield could further be attached to visor 84 by the use of double faced adhesive tape, hook and loop type fastening systems or other similar methods.

The reusable headgear of visor 84 has many features and advantages relative to either the elastic band 14 of FIG. 1 or the headgear 74 of FIG. 11. The visor 84 may be inexpensively manufactured (e.g. molded) from a suitable plastic and be used over and over again with new faceshields. This reusability will offer a more cost effective headgear relative to the disposable headgear of FIG. 11. In addition, the cost of the disposable faceshield will be lowered relative to the faceshield of FIG. 1 since the elastic strap or band increases the cost of the final product due to labor and materials to cut and attach the elastic strap to the product.

Still another feature of the headgear 84 of FIGS. 14-17 is that flange portion 96 will also offer shielding from overhead light (such as in an operating room) in addition to its function as a support for surface 30'.

Figure 2:
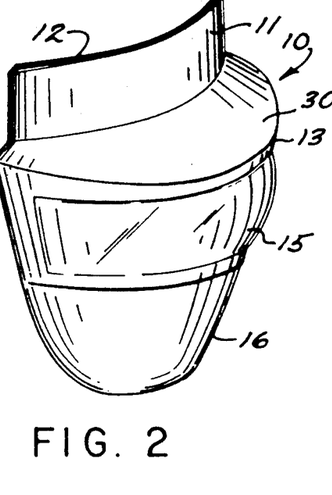
FIG. 2 is a perspective view of a preferred faceshield of the present invention with a bubble-shaped viewing area and a breath-deflecting section.
Figure 3:
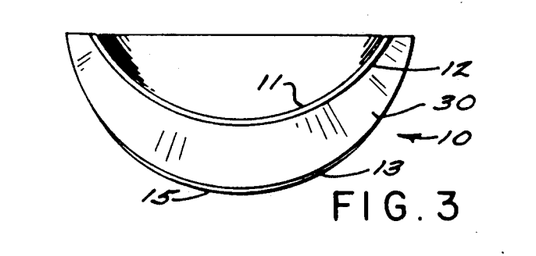
FIG. 3 is a top plan view of the faceshield illustrated in FIG. 2.
Figure 4:
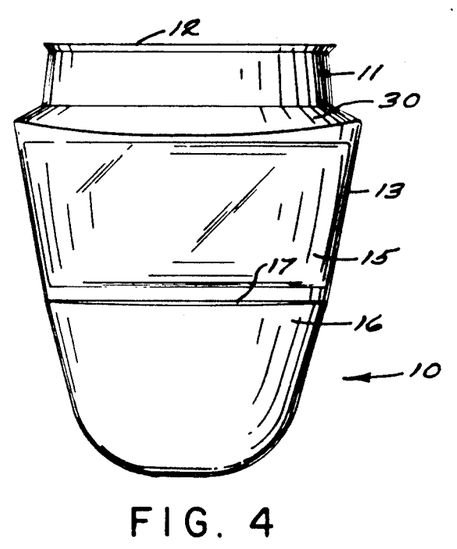
FIG. 4 is a front elevational view of the faceshield illustrated in FIG. 2.
Figure 5:
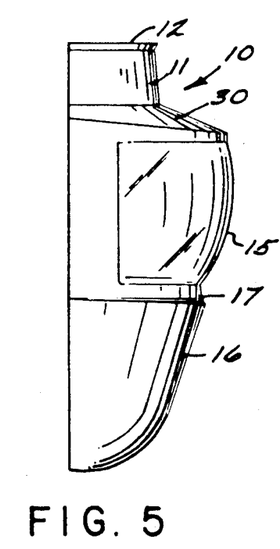
FIG. 5 is a side elevational view of the faceshield illustrated in FIG. 2.

It will be appreciated that while the headgear 74 of FIG. 11 and the headgear 84 of FIG. 14 have been shown in conjunction with the faceshield 50 of FIG. 10, headgear designs 74 or 84 may equally be used with any of the other faceshield designs depicted in FIGS. 1, 2 or 9 (goggles).

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A one piece, protective faceshield comprising:
   a curved brow member adapted to substantially conform with and contact a wearer's forehead; and
   a faceshield body extending outwardly and downwardly from said brow member along an edge and wherein said brow member and faceshield body is permanently integral along the entirety of said edge, said faceshield body being adapted to cover at least a portion of the wearer's face without contacting any part thereof below the forehead, said faceshield extending below the wearer's nose wherein said faceshield body has an upper viewing portion disposed in the wearer's viewing path and a lower portion extending outwardly and downwardly therefrom such that air exhaled by the wearer is directed away from said upper viewing portion.

2. The faceshield of claim 1 wherein:
   said brow member and faceshield is formed of a thin, transparent thermoplastic film.

3. The faceshield of claim 2 herein said thermoplastic film has a thickness less than about 0.030 inch (0.76 mm).

4. The faceshield of claim 3 wherein:
   said thermoplastic film has a thickness less than about 0.015 inch (0.38 mm).

5. The faceshield of claim 1 including:
   means for retaining said brow member in contact with the wearer's forehead.

6. The faceshield of claim 5 wherein said retaining means comprises:
   an elastic band affixed to said brow member, said elastic band being adapted to tightly circumscribe the wearer's head and snuggly retain said brow member in contact with the wearer's forehead.

7. The faceshield of claim 5 wherein said retaining means comprises:
   a pair of resilient arcuate arm members attached to said curved brow member.

8. The faceshield of claim 7 wherein:
   said resilient arm members terminate at reverse curve sections.

9. The faceshield of claim 7 wherein:
   said arm members are permanently attached to said brow member.

10. The faceshield of claim 9 wherein:
    said arm members are molded to said brow member.

11. The faceshield of claim 7 wherein:
    said arm members are detachably affixed to said brow member.

12. The faceshield of claim 1 wherein:
    said brow member has an uppermost edge which curves away from the wearer's forehead.

13. The faceshield of claim 1 wherein said thermoplastic film is selected from polycarbonates, polyesters, copolyesters, polyvinyl chloride, cellulose alkylates, polysulfones, polyethersulfones and polystyrenes.

14. The faceshield of claim 1 wherein said faceshield body extends below the wearer's nose.

15. The faceshield of claim 1 wherein said upper viewing portion is bubble shaped.

16. The faceshield of claim 1 wherein said bubble shaped viewing portion has opposed sides and including:
    protrusions formed in and extending from each of said opposed sides.

17. The faceshield of claim 16 wherein:
    said protrusions have a triangular cross-section.

18. The faceshield of claim 16 wherein said protrusions comprise:
    a triangularly shaped front panel;
    a triangularly shaped top panel adjacent a first edge of said front panel; and
    a rectangularly shaped rear panel adjacent a second edge of said front panel.

19. The faceshield of claim 18 wherein:
    said rear panel has the shape of a parallelagram.

20. A one piece, protective faceshield comprising:
    a curved brow member adapted to substantially conform with and contact a wearer's forehead; and
    a pair of resilient arcuate arm members affixed to said brow member, said arm members retaining said brow member in contact with the wearer's forehead;
    a faceshield body extending outwardly by and downwardly from said brow member along an edge and wherein said brow member and faceshield body is permanently integral along the entirety of said edge, said faceshield body being adapted to cover at least a portion of the wearer's face without contacting any part thereof;
    visor means, said visor means comprising a semi-circular band terminating at said pair of resilient arcuate arm members; and;
    means for detachably affixing said brow member to said visor means.

21. The faceshield of claim 20 wherein:

said visor means further includes a flared arcuate section extending outwardly from said semi-circular band.

22. The faceshield of claim 21 wherein said faceshield body includes a skirt attached to said brow member and wherein:
said flared arcuate section of said visor means has a shape which conforms to the shape of said skirt section.

23. The faceshield of claim 20 wherein said means for detachably affixing said brow member to said visor means comprises:
a plurality of protrusions extending outwardly from said visor means; and
a plurality of opening in said brow member for receiving and retaining said protrusions.

24. A one-piece eye protective shield comprising:
an eye protective member adapted to shield a wearer's eyes, said eye protective member being fabricated of a transparent thermoplastic film less than 0.030 inch (0.76 mm) thick and having an integral viewing portion disposed in the wearer's viewing path, wherein said viewing portion has retained at least the same optical clarity as the thermoplastic film from which said shield is fabricated; and
said viewing portion having a minimum resolution of 20 as determined by National Bureau of Standards Resolution Test Chart, Special Publication 374.

25. The eye protective shield of claim 24:
wherein said viewing portion is bubble shaped.

26. The eye protective shield of claim 24 wherein:
said eye protective member is formed by vacuum forming said transparent thermoplastic film over a forming mandrel.

27. The eye protective shield of claim 26 wherein:
said viewing portion is formed by allowing said transparent thermoplastic film to sag partially into a pocket within said forming mandrel without touching any part thereof.

28. The eye protective shield of claim 24 wherein:
said eye protective member is in the form of a goggle.

29. The eye protective shield of claim 24 wherein:
said eye protective member is in the form of a faceshield.

30. The eye protective shield of claim 29 further comprising:
a curved brow member adapted to conform with and contact the wearer's forehead, wherein said eye protective member is integral therewith and extends outwardly and downwardly therefrom so as not to contact any part of the wearer's face below the forehead.

31. The eye protective shield of claim 30 including:
means for retaining said brow member in contact with the wearer's forehead.

32. The eye protective shield of claim 31 wherein:
said retaining means comprises an elastic band affixed to said brow member and adapted to tightly circumscribe the wearer's head and snuggly retain said brow member in contact with the wearer's forehead.

33. The eye protective shield of claim 31 wherein said retaining means comprises:
a pair of resilient arcuate arm members attached to said curved brow member.

34. The faceshield of claim 24 wherein said viewing portion has opposed sides and including:
protrusions formed in and extending from each of said opposed sides.

35. The faceshield of claim 34 wherein said protrusions comprise:
a triangularly shaped front panel;
a triangularly shaped top panel adjacent a first edge of said front panel; and
a rectangularly shaped rear panel adjacent a second edge of said front panel.

36. The faceshield of claim 35 wherein:
said rear panel has the shape of a parallelagram.

* * * * *

UNITED STATES PATENT AND TRADEMARK OFFICE
CERTIFICATE OF CORRECTION

PATENT NO. : 5,088,114

DATED : Feb. 18, 1992

INVENTORS : Arthur J. Salce and Richard T. Metcalfe

It is certified that error appears in the above-identified patent and that said Letters Patent is hereby corrected as shown below:

Col. 1, Rows 20-21: The word viewing is hyphenated as "vie-wing", and should be hyphenated as "view-ing"

Col. 3, line 18: Change "faceshield to" to -- faceshield of--.

Col 4, line 9: Between "retains" and "good", delete "a".

Col 4, line 11: "20" should not be bolded, as it does not reference a figure.

Col 4, line 12: "24" should not be bolded, as it does not reference a figure.

Col 5, line 9: "8010" should not be bolded, as it does not reference a figure.

Col. 5, line 11: Delete "Copolyesters" and insert therefore -- Copolyester --.

Col 5, line 13: Between "0.030" and "inch", delete ",".

Col. 6, line 23: Delete "ultrsonic" and insert therefore --ultrasonic--.

UNITED STATES PATENT AND TRADEMARK OFFICE
CERTIFICATE OF CORRECTION

PATENT NO. : 5,088,114
DATED : February 18, 1992
INVENTOR(S) : Arthur J. Salce, et al.

It is certified that error appears in the above-indentified patent and that said Letters Patent is hereby corrected as shown below:

Col. 8, line 56, delete "by".

Signed and Sealed this

Seventh Day of September, 1993

Attest:

BRUCE LEHMAN

Attesting Officer

Commissioner of Patents and Trademarks